US008251943B1

(12) United States Patent
Spencer et al.

(10) Patent No.: US 8,251,943 B1
(45) Date of Patent: Aug. 28, 2012

(54) VASCULAR SHUNT

(75) Inventors: Jerry R. Spencer, Rio Medina, TX (US); Todd E. Rasmussen, Fair Oaks Ranch, TX (US); Shaun M. Gifford, San Antonio, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 367 days.

(21) Appl. No.: 12/652,981

(22) Filed: Jan. 6, 2010

(51) Int. Cl.
*A61M 19/00* (2006.01)
(52) U.S. Cl. .............................. 604/8; 604/9; 604/96.01
(58) Field of Classification Search ............... 604/7–10, 604/96.01; 606/153
See application file for complete search history.

(56) References Cited

U.S. PATENT DOCUMENTS

| | | | |
|---|---|---|---|
| 5,807,356 A | 9/1998 | Finch, Jr. et al. | |
| 6,019,788 A | 2/2000 | Butters et al. | |
| 6,086,553 A | 7/2000 | Akbik | |
| 6,095,997 A * | 8/2000 | French et al. | 604/9 |
| 6,139,517 A | 10/2000 | Macoviak et al. | |
| 6,214,022 B1 * | 4/2001 | Taylor et al. | 606/153 |
| 6,926,690 B2 | 8/2005 | Renati | |
| 6,966,887 B1 | 11/2005 | Chin | |
| 7,335,215 B2 * | 2/2008 | Buckman et al. | 606/153 |
| 2006/0064159 A1 * | 3/2006 | Porter et al. | 623/1.24 |
| 2008/0046073 A1 | 2/2008 | Elshire | |

OTHER PUBLICATIONS

S. Gifford et al., "Early Versus Delayed Restoration of Flow with Temprary Vascular Shunt Reduces Circulating Markers of Injury in a Porcine Model", The Journal of TRAUMA® Injury, Infection, and Critical Care, Aug. 2009, vol. 67, No. 2, pp. 259-265.
T. Rasmussen et al., "The Use of Temporary Vascular Shunts as a Damage Control Adjunct in the Management of Wartime Vascular Injury", The Journal of TRAUMA® Injury, Infection, and Critical Care, Jul. 2006, vol. 61, No. 1, pp. 8-15.
J. Taller et al., "Temporary Vascular Shunts as Initial Treatment of Proximal Extremity Vascular Injuries During Combat Operations: The New Standard of Care at Echelon II Facilities?", The Journal of TRAUMA® Injury, Infection, and Critical Care, Sep. 2008, vol. 65, No. 3, pp. 595-603.
A. Subramanian et al., "A Decade's Experience with Temporary Intravascular Shunts at a Civilian Level I Trauma Center", The Journal of TRAUMA® Injury, Infection, and Critical Care, Aug. 2008, vol. 65, No. 2, pp. 316-326.
D. Dawson et al., "Temporary Arterial Shunts to Maintain Limb Perfusion after Arterial Injury: an Animal Study", J. Trauma, Jul. 1999, vol. 47, No. 1, pp. 64-71.
Colas, Andre et al, "Silicone Biomaterials: History and Chemistry & Medical Applications of Silicones," Reprint from Biomaterials Science: An Introduction to Materials in Medicine, 2nd Ed., pp. 80-86 and 697-707, original publication date Jul. 29, 2004, Elsevier Inc.

* cited by examiner

*Primary Examiner* — Leslie Deak
(74) *Attorney, Agent, or Firm* — AFMCLO/JAZ; Rebecca Greendyke

(57) ABSTRACT

A novel shunt comprises: a first lumen having a first end and a second end, wherein the first lumen is composed of a polydimethylsiloxane material; a bulb-shaped portion positioned on each of the first end and the second end; a reinforcing spring extending along the first lumen from the first end and the second end; and a second lumen having a first end and a second end, wherein the first end is connected to a center portion of the first lumen and the second end is connected to a valve.

23 Claims, 2 Drawing Sheets

VASCULAR SHUNT

RIGHTS OF THE GOVERNMENT

The invention described herein may be manufactured and used by or for the Government of the United States for all governmental purposes without the payment of any royalty.

TECHNICAL FIELD

This disclosure relates generally to shunts. In particular, it relates to shunts for vascular injuries.

BACKGROUND

Shunts have found increased use in the treatment of traumatic vascular injuries and the like, particularly as a result of activities in Iraq and Afghanistan. In such circumstances, shunts are used to treat combat-related vascular injuries. Shunts in the arterial position allow for perfusion of the extremity during transport or fixation of associated orthopedic injuries. For injury patterns involving an artery and vein, shunts placed in the venous position provide drainage and decrease venous hypertension that can compound tissue ischemia and bleeding.

In many cases, shunts are used to treat vascular injuries resulting from improvised explosive devices, explosive munitions, high velocity weapons, and other high energy trauma. In such circumstances, shunts provide a damage control adjunct that can be applied at forward echelon locations to restore fluid flow and the like until such injuries can be treated more fully at medical treatment facilities.

The temporary shunts currently employed in these situations provide some advantages but suffer from several deficiencies. Reports from wartime and civilian medical centers confirm the effectiveness of temporary vascular shunting in the setting of vascular injury; however, these same reports describe random use of a number of devices, none of which are designed for treating vascular injuries. As such, currently available shunts are of suboptimal size, length, and diameter. Moreover, they have no capability for injection into the injured vessel and have no name recognition among trauma surgeons. Many of the currently used shunt technologies were designed and approved for use in carotid surgery for perfusion of the brain for a short period of time, rather than for temporary use in complex trauma-related vascular injury. They provide poor patency, and are not of comparable vessel size which leads to a reduction in efficacy, even for temporary use. As a result of these and other problems, the shunts currently used to treat traumatic vascular injuries are difficult to use and insert into damaged blood vessels. Similarly, in the case of the Vascutek® shunt that recently received FDA approval for use in trauma-related vascular injury, military surgeons report undesired complications because the shunt lacks the features necessary for appropriate trauma-related care. These limitations result, at least in part, from the fact that these shunts were not designed to treat traumatic vascular injuries. In aggregate, these deficiencies in technology generate the need for a trauma-specific extremity vascular shunt.

SUMMARY

The shunts disclosed herein overcome these limitations and provide vastly improved treatment for vascular injury and similar trauma. These shunts, referred to as trauma specific-vascular injury shunts (TS-VIS), provide a short-term (<24 hours) implantable device that can be used by qualified medical personnel to temporarily restore blood flow to a person's injured extremity following a complex trauma-related vascular injury. The TS-VIS can remain in place for several hours or longer to restore perfusion in the affected body area until the patient can be transported to a tertiary care or similar medical treatment facility where a permanent vascular repair can be accomplished, at which time the TS-VIS is removed. The TS-VIS is designed for use by qualified medical personnel. It can be used to treat military and civilian trauma-related vascular injuries and it significantly improves the salvage of damaged limbs by restoring and maintaining the flow of blood and fluid to those limbs until the vascular injuries can be permanently repaired.

The TS-VIS includes unique novel features for treating traumatic vascular injuries to create a device optimally designed for temporary traumatic vascular injury repair. As such, it provides a single shunt that is designed for treatment of vascular injury and can be recognized and used by trauma surgeons and other trained medical personnel to treat traumatic vascular injuries, thus ending the current use of a myriad of suboptimal, non-trauma devices.

The TS-VIS represents an important breakthrough in the management of extremity blood vessel trauma. The improved design enables medics and others to properly insert TS-VIS shunts to restore blood flow in damaged blood vessels. It also enables unit-level medics and others to treat patients with traumatic vascular injuries at the scene of the injury or trauma and restore blood flow until patients are transported to medical treatment facilities for surgery and repair of those injuries. As a result of the use of the TS-VIS, unnecessary loss of limb and other injuries can be avoided.

In one embodiment, a shunt comprises: a first lumen having a first end and a second end, wherein the first lumen is composed of a polydimethylsiloxane material; a bulb-shaped portion positioned on each of the first end and the second end; a reinforcing spring extending along the first lumen from the first end and the second end; a second lumen having a first end and a second end, wherein the first end is connected to a center portion of the first lumen and the second end is connected to a valve.

In another embodiment, a method of repairing a damaged vessel with a temporary vascular injury shunt comprises the steps of: inserting a bulb-shaped portion at one end of the shunt into one portion of the damaged vessel; inserting a bulb-shaped portion at the other end of the shunt into the other portion of the damaged vessel; securing each of the bulb-shaped portions within the respective portions of the damaged vessel by a clip, a rubber band, vessel loops, and/or a suture; and pulling the shunt away from each portion of the damaged vessel so that the clip, the rubber band, the vessel loop, and/or the suture is adjacent to each bulb-shaped portion.

In a further embodiment, a method of treating traumatic vascular injuries, comprises the steps of: inserting the first end and the second end of the shunt into respective portions of a damaged vessel; securing the first and second ends of the shunt in the respective portions of the damaged vessel; monitoring the flow of blood through the shunt; providing blood, medicine, contrast, media, and/or other fluid to the traumatic vascular injury via the shunt; transporting the patient to a medical treatment facility; and permanently repairing the traumatic vascular injury.

DETAILED DESCRIPTION

Figure 1:
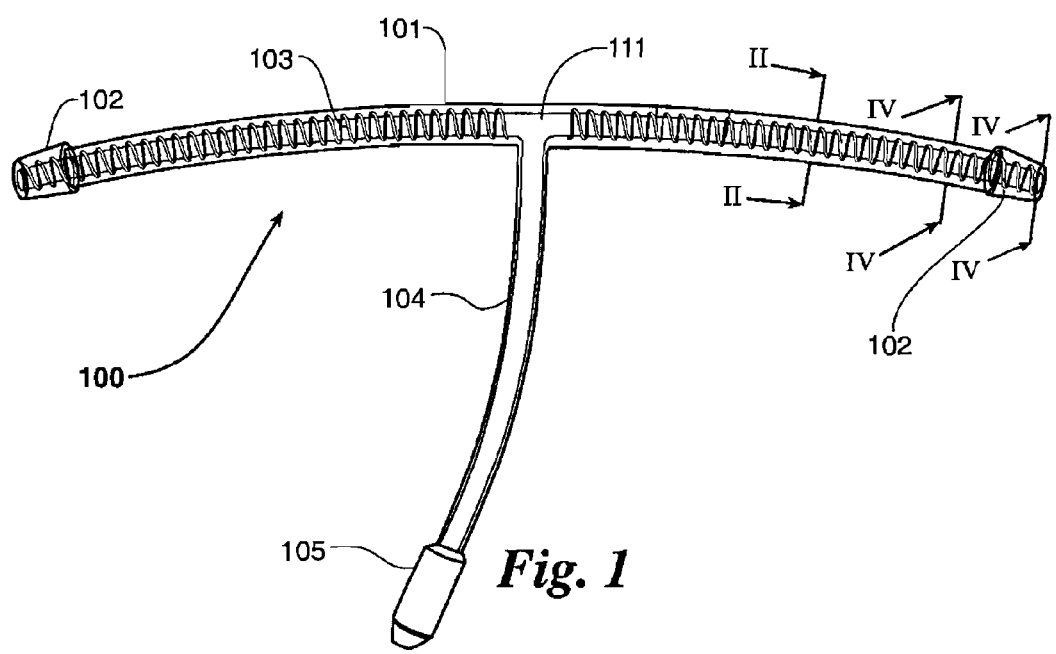
FIG. 1 discloses an embodiment of a shunt.
Figure 4:
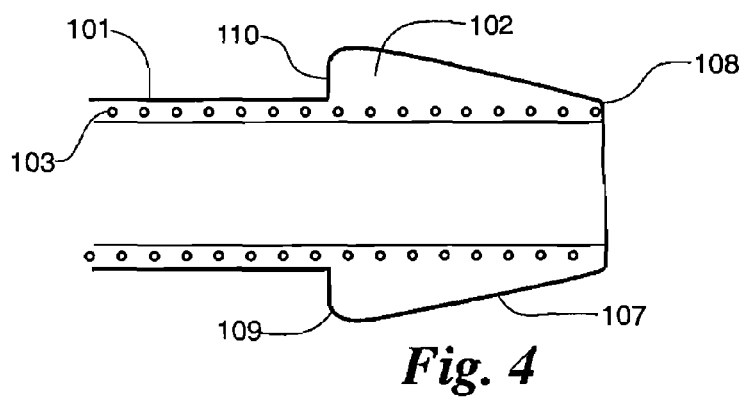
FIG. 4 is a side cross-sectional view taken along line IV-IV of FIG. 1.

In one embodiment, a TS-VIS 100 includes a first lumen 101, a bulb-shaped portion 102 positioned on each end of the first lumen 101, a reinforcing spring 103 disposed within the first lumen 101, and a second lumen 104 with a valve 105, as shown in FIG. 1. The first lumen 101 comprises a medical grade tubing made of a biocompatible platinum-catalyzed polydimethylsiloxane (PDMS) material. This material is generally clear so medical personnel and others can monitor the flow of blood through the TS-VIS 100 visually and use Doppler instruments to measure blood flow through the TS-VIS 100. This material also makes the TS-VIS 100 rigid enough so that it retains its shape during and after insertion, but also is flexible enough to give the TS-VIS 100 the capability of being manipulated during insertion. This material also provides improved patency and eliminates clotting that occurs in shunts made of other materials, such as polytetrafluoroethylene (PTFE) and expanded polytetrafluoroethylene (ePTFE). In contrast, the PDMS material used in the TS-VIS 100 largely eliminates clotting.

In one embodiment, the TS-VIS 100 has a length of 30 cm. This length is well-suited for bridging missing segments of blood vessels under varied circumstances and it avoids further vessel damage that can occur from over-stretching a shunt to bridge a larger gap than the shunt was designed to handle. This length also enables medical personnel and others to connect damaged blood vessels while providing enough slack in the shunt to bridge bones and other injuries that orthopedic surgeons and others can repair without disrupting the flow of blood in the repaired vessel. This configuration also enables the TS-VIS 100 to be employed in a straight or looped configuration depending upon the nature of the injury to be treated and the gap to be bridged by the TS-VIS 100.

The bulb-shaped portions 102 are positioned on each end of the first lumen 101. The bulb-shaped portions 102 are made of a PDMS medical grade tubing or similar materials. The bulb-shaped portions 102 are configured to facilitate their insertion into a vessel insertion site. This configuration is a marked improvement over existing shunt designs and not only enables medical personnel to quickly and accurately position the TS-VIS 100 in injured vessels, but also reduces or eliminates the trauma to those vessels that typically results from the use of current shunts. The design of the bulb-shaped portions 102 also prevents clotting in repaired vessels and provides vastly increased patency in the TS-VIS 100, as compared to current shunts used to treat traumatic vascular injuries. In one embodiment, the bulb-shaped portions 102 are cone-shaped and have an outer surface 107 that tapers from an outer diameter of about 5.5 mm at the distal end 108 of the bulb-shaped portions 102 to about 6.5 mm at the proximal end 109 of the bulb-shaped portions 102. This configuration facilitates easy, atraumatic insertion of the TS-VIS 100 within a vessel and it improves shunt stability after placement, particularly under adverse conditions such as those found in combat environments and the like where patients may be in shock or experiencing extreme drops in blood pressure. It also improves the patency of the TS-VIS 100 in excess of 24 hours, if necessary. The wall thickness of the bulb-shaped portions 102 is about 1 mm. However, the configuration, shape, dimensions, and thickness of the bulb-shaped portions 102 may be varied depending on the nature of the injury to be treated. In one embodiment, the bulb-shaped portions 102 are formed integrally with the first lumen 101, for example during an extrusion process. In another embodiment, the bulb-shaped portions 102 may be formed separately and affixed to the first lumen 101, for example, by adhesive, welding, and the like.

Figure 2:
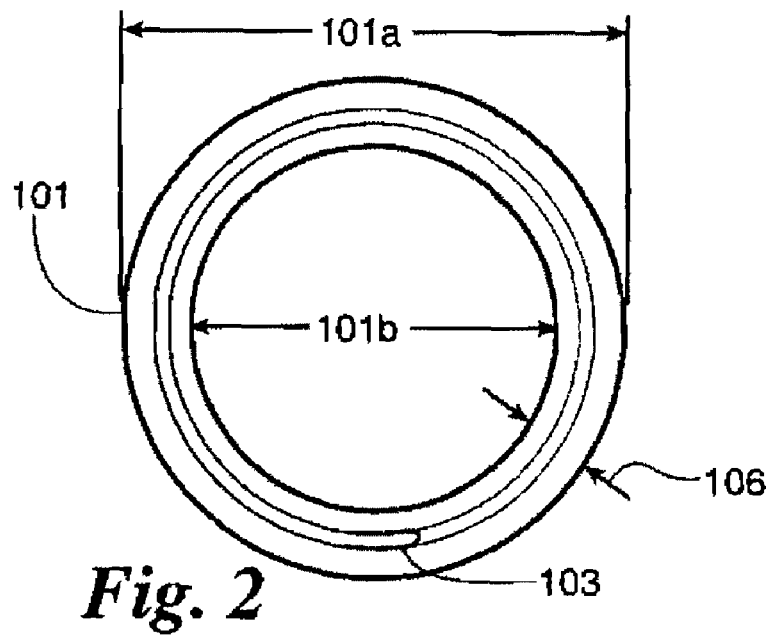
FIG. 2 is a cross-sectional view taken along line II-II of FIG. 1.

The reinforcing spring 103 is made of stainless steel or a similar material. It also may be made of a wire mesh material. The reinforcing spring 103 extends along the length of the first lumen 101 from each bulb-shaped portion 102. In one embodiment, the reinforcing spring 103 can be formed within the first lumen 101 during extrusion of the first lumen 101. The reinforcing spring 103 is disposed entirely within the first lumen 101 so that no portion of the reinforcing spring 103 extends beyond an outer surface or an inner surface of the first lumen 101, as shown in FIG. 2. In one embodiment, the reinforcing spring 103 does not extend along the entire length of the first lumen 101, so that a center portion 111 of the first lumen 101 is not reinforced by the reinforcing spring 103, as shown in FIG. 1. In this embodiment, the unreinforced center portion 111 of the first lumen 101 is about 1 cm in length. However, the non-reinforced center portion 111 of the first lumen 101 may be greater or less than 1 cm, depending on the nature of the injury to be treated and the configuration of the TS-VIS 100. The unreinforced center portion 111 provides a region on the TS-VIS 100 that medical personnel can grasp with a hemostat, forceps, clamps, or similar instrument to position the TS-VIS 100 for insertion in a vascular wound without damaging the TS-VIS 100 or impairing its patency. The reinforcing spring 103 prevents kinking of the first lumen 101 after the TS-VIS 100 is inserted into a blood vessel. It also keeps the first lumen 101 open when the TS-VIS 100 is disposed in a looped or coiled configuration. In another embodiment, the reinforcing spring 103 does not extend completely through the bulb-shaped portions 102 at the distal ends of the first lumen 101.

The second lumen 104 is attached at the center portion 111 of the first lumen 101. The second lumen 104 can be attached to the first lumen 101 by welding, melting, or other attachment means. In one embodiment, the second lumen 104 is about 10 cm long and has an outer diameter of about 3 mm, an inner diameter of about 2.5 mm, and a wall thickness of about 0.25 mm. The valve 105 is positioned on the end of the second lumen 104 that is distal to the first lumen 101. In one embodiment, the valve 105 is a one piece valve, such as a Maximus® MP1000 valve connector with a luer lock, made by Medegen, Inc., 930 South Wanamaker Avenue, Ontario, Calif. The second lumen 104 and the valve 105 provide an injection port that facilitates the injection of medications and contrast media into the TS-VIS 100 and the repaired blood vessel. This also enables medical personnel to inject de-clotting agents and medicines such as medicines for limb salvage at a site that is best suited for that injury and eliminates the need to establish an alternate port or injection site for treatment of that injury. Contrast media for angiograms and the like can be injected through the second lumen 104 without the need to insert a catheter or other device into the wound or damaged limb. The luer lock of the valve 105 provides a means to secure medicines, blood, and other fluids to the second lumen 104 without the need for medical personnel to remain on station. If the second lumen 104 is not used for injection or supply of medicines, blood, fluid, contrast media, or other fluids, the valve seals the second lumen 104. When a syringe or other instrument is connected to the valve 105, the valve opens to permit medicines, blood, fluid, contrast media, or other fluids to be supplied through the second lumen 104.

As shown in FIG. 2, the first lumen 101 has a circular or generally circular cross-section. In one embodiment, the outer diameter 101a of the first lumen 101 is about 5.5 mm and the inner diameter 101b is about 4.0 mm, producing a total wall thickness of about 1.5 mm, or a thickness in a single wall 106 of about 0.75 mm. This configuration provides improved perfusion to injured limbs while ensuring the patency of the TS-VIS 100 and avoidance of a ballooning effect in the non-reinforced portion of the first lumen 101. The configuration of the TS-VIS 100, including the outer diameter 101a, inner diameter 101b, and wall thickness 106 of the first lumen 101, may be varied depending on the nature of the injury to be treated so that the TS-VIS 100 may be used in the large arteries and veins of the proximal lower extremities and the small arteries and veins of the upper extremities. For example, a smaller unit with outer diameter 101a of the first lumen 101 is about 4.0 mm and the inner diameter 101b is about 2.5 mm, producing a wall thickness 106 of about 1.5 mm.

Figure 3:
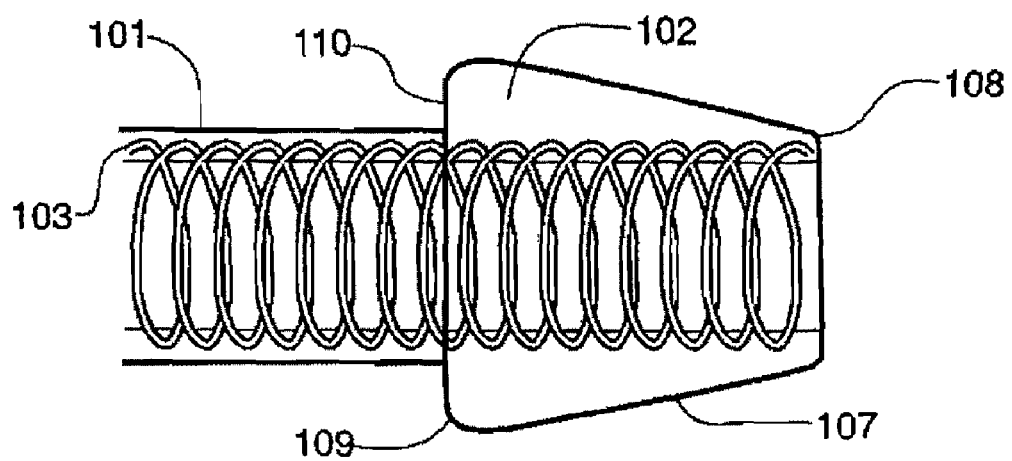
FIG. 3 is a side perspective of an expanded portion of the shunt of FIG. 1.

As shown in FIG. 3, the bulb-shaped portion 102 includes a tapered outer surface 107. In one embodiment, the tapered outer surface 107 is a continuous linear surface that tapers outwardly from an outer diameter of about 5.5 mm at the distal most portion 108 of the bulb-shaped portion 102 to an outer diameter of about 6.5 mm at the proximal most portion 109. In other embodiments, the outer surface 107 can have a non-linear tapered surface that forms, for example a regular or irregular convex or concave surface, depending upon the nature of the injury to be treated. As shown in FIG. 3, the proximal portion 109 of the bulb-shaped portion 102 has a generally straight or flat rear surface 110. In other embodiments, the rear surface 110 of the proximal outer edge 109 may have a curved configuration depending on the nature of the injury to be treated. Additionally, the curvature of the proximal portion 109 may be varied, as desired. The configuration of the TS-VIS 100, including the bulb-shaped portion 102 and the tapered outer surface 107 may be varied depending on the nature of the injury to be treated. The bulb-shaped portion 102 will have a maximum measurement of about 5.0 mm, and tapering to a wall thickness 108 of about 1.5 mm.

In one embodiment, the TS-VIS 100 can be used to repair a damaged blood vessel in the following manner. One bulb-shaped portion 102 of the TS-VIS 100 is inserted into one portion of the damaged blood vessel. Then, the other bulb-shaped portion 102 is inserted into the other portion of the damaged blood vessel. An elastic or rubber band, clip, vessel loops, and/or a suture is then wrapped around the outer surface of each portion of the damaged vessel behind the proximal portion 109 of each bulb-shaped portion 102. This causes the blood vessel to be drawn inward behind the proximal portion 109 of each bulb-shaped portion 102, adjacent to the rear surface 110 to secure each bulb-shaped portion 102 of the TS-VIS 100 within the respective portion of the damage blood vessel. After the ends of the damaged blood vessel are clipped or secured around the bulb-shaped portions 102, each bulb-shaped portion 102 can be slid back against the bands or clips to secure the TS-VIS 100 inside the respective portions of the blood vessel with the rear surfaces 110 of each bulb-shaped portion 102 adjacent to the clipped or banded portion of the damaged vessel. This also minimizes the portion of the TS-VIS 100 that is disposed within the damaged vessel to the minimum amount needed to secure the TS-VIS 100 and restore blood flow. If the length of the TS-VIS 100 exceeds the length needed to bridge the gap in the damaged blood vessel, the first lumen 101 can be coiled in a looped or S-shaped configuration. This capability permits surgeons and other medical personnel to examine and repair bone, tissue, and other damaged portions of the wound without disrupting the flow of blood through the repaired vessel. It also permits patients to be transported from injury sites to medical treatment facilities without the TS-VIS 100 becoming kinked or losing its patency during transport. Because the PDMS material of the TS-VIS 100 is clear, visual observation can be made of the flow of blood through the TS-VIS 100 and the repaired vessel. In addition, blood flow through the TS-VIS 100 and the repaired vessel also can be monitored by Doppler instruments. After the patient is transported to a medical treatment facility, surgeons can repair broken bones and other damaged tissue while the TS-VIS 100 maintains perfusion to the injured limb, thereby reducing the incidence of limb loss and further injury. After bones and other trauma have been repaired, the damaged vessel can be permanently repaired, for example with a permanent graft of piece of vein and the like. The TS-VIS 100 may be removed to facilitate permanent repair of the damaged vessel.

The foregoing disclosure has been presented for purposes of illustration and description and is not intended to be exhaustive or to limit the invention to the various embodiments and forms disclosed herein. Persons skilled in the art will realize and appreciate that many modifications and variations are possible in light of the above teaching. For example, the design, configuration, dimensions, and materials of the TS-VIS may be varied, as desired, depending on the application and intended use of the shunts. The disclosed embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A trauma-specific vascular injury shunt comprising:
    a first lumen having a first end and a second end, wherein the first lumen is composed of a polydimethylsiloxane material;
    a bulb-shaped portion positioned on each of the first end and the second end;
    a reinforcing spring extending along the first lumen from the first end and the second end; and
    a second lumen having a first end and a second end, wherein the first end is connected to a center portion of the first lumen and the second end is connected to a valve;
    wherein the polydimethylsiloxane material is a biocompatible platinum-catalyzed polydimethylsiloxane.

2. The trauma-specific vascular injury shunt of claim 1, wherein the polydimethylsiloxane material is generally clear to facilitate visual observation of blood flow through the trauma-specific vascular injury shunt.

3. The trauma-specific vascular injury shunt of claim 1, wherein the reinforcing spring does not extend through a center portion of the first lumen to facilitate a measurement of blood flow through the trauma-specific vascular injury shunt via a Doppler instrument and to allow clamping ability without the need for shunt removal or risk of damaging the reinforcing spring.

4. The trauma-specific vascular injury shunt of claim 1, wherein the first lumen is generally linear in shape and has an outer diameter of about 5.5 millimeters and an inner diameter of about 4.0 millimeters.

5. The trauma-specific vascular injury shunt of claim 1, wherein the valve is a one-piece luer connector valve.

6. The trauma-specific vascular injury shunt of claim 1, wherein each bulb-shaped portion has a cone-shaped configuration that tapers outwardly from a distal portion of each bulb-shaped portion to a proximal portion of each bulb-shaped portion.

7. The trauma-specific vascular injury shunt of claim 6, wherein the cone-shaped configuration tapers from about a 5.5 outer diameter at the distal portion to a 6.5 millimeter outer diameter at the proximal portion.

8. The trauma-specific vascular injury shunt of claim 1, wherein the reinforcing spring is positioned within the first lumen so that no portion of the reinforcing spring extends beyond an inner surface or an outer surface of the first lumen.

9. The trauma-specific vascular injury shunt of claim 1, wherein the reinforcing spring is made of stainless steel and extends from the first end and the second end of the first lumen to an unreinforced center portion of the first lumen.

10. The trauma-specific vascular injury shunt of claim 9, wherein the unreinforced center portion of the first lumen is about 1 cm in length.

11. The trauma-specific vascular injury shunt of claim 1, wherein the second lumen is attached to the first lumen at the center portion of the first lumen by at least one of adhesive, welding, and molded one piece extrusion.

12. The trauma-specific vascular injury shunt of claim 1, wherein the second lumen is in fluid communication with the first lumen and provides an injection port for at least one of medicines, de-clotting agents, contrast media, and blood.

13. The trauma-specific vascular injury shunt of claim 1, wherein the first lumen is capable of being coiled into a looped or S-shaped configuration.

14. The trauma-specific vascular injury shunt of claim 1, wherein the first lumen can remain patent for periods exceeding 24 hours after being inserted into a damaged blood vessel.

15. The trauma-specific vascular injury shunt of claim 1, wherein the bulb-shaped portion is formed integrally on the first end and the second end of the first lumen.

16. A method of repairing a damaged vessel with the trauma-specific vascular injury shunt of claim 1 comprising the steps of:
   inserting the bulb-shaped portion positioned at the first end of the first lumen into one portion of the damaged vessel;
   inserting the bulb-shaped portion positioned at the second end of the first lumen into another portion of the damaged vessel;
   securing each of the bulb-shaped portions within each respective portion of the damaged vessel by at least one of a clip, a rubber band, vessel loops, and suture, wherein the clip, the rubber band, the vessel loops, and/or the suture are wrapped around an outer vessel surface of each portion of the damaged vessel; and
   pulling the trauma-specific vascular injury shunt away from each respective portion of the damaged vessel so that the clip, the rubber band, the vessel loops and/or the suture is adjacent to each bulb-shaped portion.

17. The method of claim 16, further comprising the step of coiling the trauma-specific vascular injury shunt into a looped or S-shaped configuration after placement of each of the bulb-shaped portions within each respective portion of the damaged vessel, wherein the reinforcing spring keeps the first lumen patent and prevents the first lumen from kinking.

18. The method of claim 16, further comprising the step of transporting a patient to a medical treatment facility, repairing non-vascular injuries prior to repairing the damaged vessel, and removing the trauma-specific vascular injury shunt and repairing the damaged vessel permanently.

19. The method of claim 16, further comprising the step of grasping the trauma-specific vascular injury shunt at the center portion of the first lumen with at least one of a hemostat, a clamp, and forceps and positioning the trauma-specific vascular injury shunt over the damaged vessel to facilitate insertion of the bulb-shaped portions into the respective portions of the damaged vessel to be repaired.

20. The method of claim 16, further comprising the step of supplying at least one of medicine, de-clotting agents, blood, and contrast media to the damaged vessel via the valve connected to the second end of the second lumen, the second lumen being in fluid communication with the first lumen.

21. A method of treating traumatic vascular injuries in a patient, comprising the steps of:
   inserting the first end and the second end of the first lumen of the trauma-specific vascular injury shunt of claim 1 into respective portions of a damaged vessel;
   securing the first and second ends of the first lumen in the respective portions of the damaged vessel, wherein at least one of a clip, a rubber band, vessel loops, and a suture are wrapped around an outer vessel surface of each portion of the damaged vessel;
   monitoring blood flow through the trauma-specific vascular injury shunt by visual monitoring and by measuring the blood flow via a Doppler instrument;
   providing at least one of blood, medicine, de-clotting agents, and contrast media to the traumatic vascular injury via the valve connected to the second end of the second lumen;
   transporting the patient to a medical treatment facility; and
   permanently repairing the traumatic vascular injury.

22. The method of claim 21, further comprising the step of repairing a non-vascular injury at the medical treatment facility before permanently repairing the traumatic vascular injury.

23. The method of claim 21, further comprising the step of coiling the trauma-specific vascular injury shunt into a looped or S-shaped configuration after placement of the first end and second end of the first lumen into the respective portions of the damaged vessel to facilitate patency of the trauma-specific vascular injury shunt during transport of the patient to a medical treatment facility and to permit access to areas adjacent to the damaged vessel without disrupting blood flow through the trauma-specific vascular injury shunt, wherein the reinforcing spring keeps the first lumen patent and prevents the first lumen from kinking

* * * * *